United States Patent [19]

Merianos et al.

[11] Patent Number: 4,954,636
[45] Date of Patent: Sep. 4, 1990

[54] ANTIMICROBIAL POLYMERIC BISBIGUANIDES

[75] Inventors: John J. Merianos, Middletown; Paul Garelick, South Plainfield, both of N.J.

[73] Assignee: GAF Chemicals Corporation, Wayne, N.J.

[21] Appl. No.: 374,891

[22] Filed: Jul. 3, 1989

[51] Int. Cl.$^5$ .................. C07D 207/12; C07C 279/12; C07C 277/08
[52] U.S. Cl. ..................................... 548/519; 564/233
[58] Field of Search .......................... 564/233; 548/519

[56] References Cited

U.S. PATENT DOCUMENTS

| | | | |
|---|---|---|---|
| 3,468,898 | 9/1969 | Cutler et al. | 564/233 |
| 4,022,834 | 5/1977 | Gundersen et al. | 564/233 |
| 4,567,174 | 1/1986 | Edwards et al. | 514/210 |
| 4,670,592 | 6/1987 | Eakin et al. | 544/86 |

FOREIGN PATENT DOCUMENTS 149827 2/1953 Australia ............................. 564/233

Primary Examiner—Mukund J. Shah
Assistant Examiner—E. C. Ward
Attorney, Agent, or Firm—Walter Katz; Marilyn J. Maue; Joshua J. Ward

[57] ABSTRACT

Antimicrobial polymeric bisbiguanides capped with alkylene pyrrolidonyl groups having the formula:

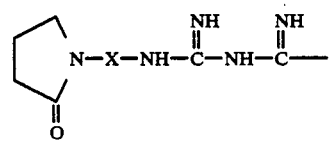

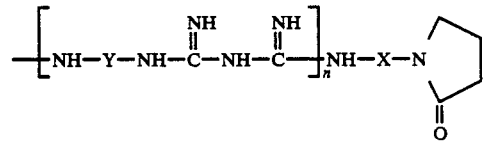

where X is $C_2$-$C_4$ alkylene; Y is a bivalent bridging group; and n is at least 2; and acid addition salts thereof.

24 Claims, No Drawings

ANTIMICROBIAL POLYMERIC BISBIGUANIDES

BACKGROUND OF THE INVENTION

1. Field of the Invention

This invention relates to antimicrobial polymeric bisbiguanides, and, more particularly, to antimicrobial polymeric bisbiguanides capped with alkylene pyrrolidonyl groups.

2. Description of the Prior Art

Bisbiguanides are well known as antimicrobial agents. See, for example, U.S. Pat. Nos. 3,468,898; 4,022,834; 4,567,174; and 4,670,592. Manufacture of antimicrobial polymeric diguanides by reaction of a metal salt of dicyanamide, or a diamine salt of dicyanamide, and a diaminoalkane, has been described in U.S. Pat. Nos. 2,643,232 and 3,428,576. Polymeric diguanides based upon these patents have broad spectrum biocidal activity and have gained wide acceptance as disinfectants in the brewing, foodstuff, soft drink and dairy industries. For example, Vantocil® IB, a trademark of the ICI Corp., is a cationic polymeric diguanide which is an active disinfectant for use in these industries. However, the presence of cyano and/or amino end groups in these polymers can contribute to their toxicity and/or irritability.

Cutler, in Soap and Chemical Specialties, February 1966, page 45, relates effective antimicrobial activity of bisbiguanides to their hydrophilic-lipophilic balance (HLB) values. However, since bacteria grows in an aqueous phase, preferred antimicrobial bisbiguanides should have water solubility as well as suitable HLB values.

Accordingly, it is an object of the invention to provide novel antimicrobial polymeric bisbiguanides which have excellent water solubility, and reduced toxicity and irritability properties.

These and other objects and features of the invention will be made apparent from the following more particular description thereof.

SUMMARY OF THE INVENTION

In accordance with the object of the invention, there is provided herein antimicrobial bisbiguanide polymers capped with alkylene pyrrolidonyl groups. These compounds have Formula I given below:

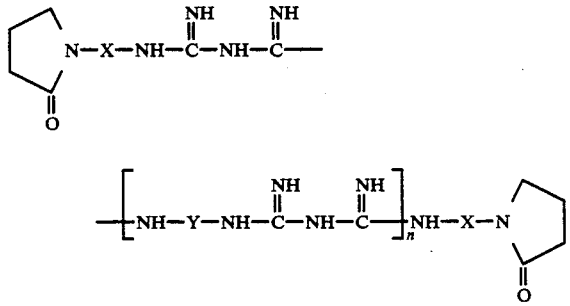

where X is $C_2$–$C_4$ alkylene; e.g. ethylene, propylene and butylene;

Y is a bivalent bridging group selected from alkylene, or alkylene interrupted with oxygen, and also may incorporate cyclic nuclei which themselves may be saturated or unsaturated, and mixtures thereof; and n is at least 2, e.g. 2–15; preferably 4–11; and inorganic and organic acid addition salts thereof.

The presence of the water solubilizing, non-toxic, non-irritating alkylene pyrrolidonyl capping groups in the polymeric bisbiguanides of the invention enhances their water solubility and decreases their toxicity and irritability, as compared to related polymeric compounds which have cyano and/or amino end groups present.

DETAILED DESCRIPTION OF THE INVENTION

Antimicrobial bisbiguanide polymers capped with alkylene pyrrolidonyl groups may be made by a one-pot, 2-step process. The first step involves condensing sodium dicyanamide, or a bis-(cyanoguanido)alkane, with a salt of a suitable diamine, $H_2N$-Y-$NH_2$, where Y is a bridging group. For example, a diaminoalkane, or a diaminoalkane interrupted with an oxygen, may be used. Representative diamine compounds for use herein include (a) 1,6-diaminohexane; (b) 1,12-diaminododecane;
(c) 1,5-diamino-2-methylpentane; and
(d) 1,2-bis(-2-aminoethoxy) ethane; and mixtures thereof;

preferably in the form of their inorganic or organic acid addition salts, such as the hydrochloride, acetate, etc. Such diamines have the formulas:

(a) $H_2N$-$(CH_2)_6$-$NH_2 \cdot 2HCl$
(b) $H_2N$-$(CH_2)_{12}$-$NH_2 \cdot 2HCl$

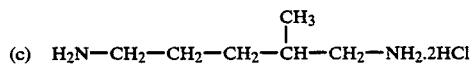

(d) $H_2N$-$CH_2CH_2OCH_2CH_2OCH_2CH_2$-$NH_2 \cdot 2HCl$

A typical bis-(cyanoguanido)-alkane is 1,6-bis(-cyanoguanido)hexane.

A blend of several diamine dihydrochlorides within a predetermined compositional range also may be used in this reaction in place of a single diamine. Such diamine mixtures will form polymers with mixed bridging groups having different hydrophilic-lipophilic balance (HLB) values. For example, alkylene bridging groups provide lipophilic activity while oxygen interrupted alkylene groups provide hydrophilic activity. Thus, diamine mixtures with both alkylene and oxygen interrupted alkylene groups, in a predetermined ratio, will provide polymeric compounds having selected HLB values characteristic of the particular mixture of diamines.

The condensation reaction in step one is carried out between the dicyanamide salt, or bis-cyanoguanidoalkane, and diamine dihydrochloride reactants using a small excess (about 5–10%) of the dicyanamide or bis-cyanoguanidoalkane compound over the stoichiometric molar ratio of 1:1 required to form the polymeric intermediate. This excess ensures a substantially complete cyano end grouping (no amino) in the condensation polymeric intermediates formed during the reaction. Preferably this step is carried out in two stages. The first stage involves a stoichiometric reaction between the reactants. The second stage involves addition of the desired excess of the dicyanamide or bis-cyanoguanidoalkane reactant.

The second step in the process comprises reacting the cyano end groups of the polymeric intermediate with an aminoalkylene pyrrolidone salt. This reaction forms the biguanido groups of the polymer product and provides the desired alkylene pyrrolidonyl capping groups. This step, also, is carried out with a small excess (about 5–10%) of the aminoalkylene pyrrolidone hydrochloride reactant over stoichiometry. Accordingly, substantially complete reaction of the cyano end groups in the polymeric intermediate with aminoalkylene pyrrolidone is achieved and the polymeric product does not contain any detectable amount of toxic (cyano) or irritating (amino) end groups.

The polymeric compounds of the invention may have the same or different Y bridging groups. Different groups may be obtained from a mixture of different diamine dihydrochloride reactants, or by using a biscyanoguanidoalkane which has an alkane group different from the diamine dihydrochloride reactant.

The invention will now be illustrated by reference to the following examples.

EXAMPLE 1

A reaction flask equipped with a condenser, thermometer, mechanical stirrer and heating mantle was charged with:

Step 1(a)

1,6-hexamethylenediamine dihydrochloride, 37.8 g. (0.20 mole);
17.8 g. (0.20 mole) of sodium dicyanamide; and 250 ml. of n-butanol.

The reaction slurry then was heated to reflux at 120° C. for 8–12 hours.

Step 1(b)

To the above refluxed reaction mixture, 4.5 g. (0.05 mole) of sodium dicyanamide was added and the reaction mixture was refluxed again for another 8–12 hours.

Step 2

16.4 g. (0.10 mole) of aminoethyl pyrrolidone hydrochloride then was added and the mixture was refluxed at 120° C. for 8–12 hours. A solid product formed (11.95 g. of NaCl) which was filtered and washed with butanol. The butanol solution then was concentrated on a rotary evaporator (90 mm, 100° C.) to remove the solvent.

The viscous residue then was dissolved in methanol, and the desired product was precipitated from 1000 ml. of acetone as a white hygroscopic solid (60.5 g., 96.8% yield).

The structure of the polymer product was determined by instrumental analysis. The IR spectra showed the absence of a detectable amount of cyano groups characteristic of the starting materials. NMR and C-13 analysis confirmed the structure of the polymer as being that of Formula I above. The molecular weight of the polymer was determined by HPLC, as giving an n value of 7–8; and it was in agreement with the stoichiometry indicated by the ratio of the reactants used.

EXAMPLE 2

Example 1 was repeated using the following materials:

54.6 g. (0.20 mole) of 1,12-dodecanediamine·2HCl
19.7 g. (0.22 mole) of sodium dicyanamide;
250 ml. of n-butanol; and
6.91 g. (0.042 mole) of aminoethyl pyrrolidone hydrochloride.

The resultant polymeric bisguanide product had a 1,12-dodecane bridging group, and a molecular weight corresponding to n=5–7.

EXAMPLE 3

The procedure and amounts used in Example 1 was followed using: 1,5-(2-methyl) pentane diamine dihydrochloride as the diamine starting material. The resulting polymeric bisguanide had a bridging group characteristic of this diamine.

EXAMPLE 4

The procedure of Example 1 was followed using a mixture of the following diamines:

1,6-hexamethylenediamine·dihydrochloride, 9.45 g. (0.05 mole);
1,2-bis-(2-aminoethoxy)ethane dihydrochloride, 22.10 g. (0.10 mole); and 1,12-dodecanediamine dihydrochloride; 13.65 g. (0.05 mole);
(a total of 0.20 mole of the mixture of diamine dihydrochlorides); with
20.30 (0.228 mole) of sodium dicyanamide; 250 ml. of n-butanol; and
13.2 g. (0.08 mole) of aminoethyl pyrrolidone·HCl.

58.7 g. (yield 96%) of a polymeric product was obtained which contained mixed bridging groups characteristic of the diamines used, in the proportions charged. The product was purified and analyzed as in Example 1. The molecular weight (n=9–11) of the purified polymeric bisguanide was in agreement with the stoichiometry indicated by the ratio of reactants used.

EXAMPLE 5

The procedure of Example 1 was followed using:

Step 1(a)

1,6-bis(cyanoguanido) hexane* 25.0 g. (0.1 mole)
1,6-hexamethylenediamine·2HCl 18.9 g. (0.1 mole)
n-butanol 200 ml.
Heat the mixture for 12 hours at 120° C.

Step 1(b)

Add 1,6-bis(cyanoguanido) hexane 5.0 g. (0.02 mole) and
Heat for 12 hours at 120° C. * This starting material was prepared by heating 189 g. (1 mole) of 1,6-hexamethylene diamine·2HCl with 180 g. (2 moles) of sodium dicyanamide in 600 ml. butanol to reflux at 120° C. for 6 hours. The precipitate was filtered, washed with butanol, and suspended in water to dissolve the NaCl. Filtration yields 242 g. of the compound, m.p. 198°−202° C.

Step (2)

Add N-(2-aminoethyl) pyrrolidone·HCl 8.2 g. (0.05 mole).
Heat for 12 hours at 120° C.

The reaction product then was cooled to form a fine white precipitate which was filtered and 1.5 g. of NaCl was removed. The butanol was evaporated under vacuum. A viscous semi-solid residue formed which was dissolved in methanol (100 ml.) and the product was precipitated with 1000 ml. of acetone. The polymeric product (54.5 g.) (yield of 95%) as the hydrochloride salt was dried in a vacuum dessicator. The molecular weight (n=9–11) of the polymer was characteristic of the starting materials and proportions used.

PROPERTIES OF POLYMERS

The polymeric bisbiguanide compounds of the present invention exhibit the antimicrobial properties characteristic of the biguanide structure and are water soluble, non-toxic, and non-irritating. Such properties are particularly advantageous in use as surgical scrub compositions. In such use, the antimicrobial action of the polymer can be effected without absorption of the compound by the skin of the user.

The antimicrobial efficacy of the compounds herein are consistent with related biguanides, such as chlorhexidine, which have a minimum inhibitory concentration, (MIC), required to kill gram positive and gram negative bacteria, of about 10–100 ppm. However, the polymeric bisbiguanides of the invention are expected to be less toxic and less irritating than chlorhexidine or related biguanide compounds containing cyano and/or amino end groups. Accordingly, they will require a somewhat higher MIC level, e.g. 100–250 ppm, to achieve similar activity. The somewhat lower antibacterial activity, however, is accompanied by increased safety in use.

Although the invention has been described with reference to certain embodiments thereof, it will be understood that changes and modifications may be made which are consistent with the skill of the art. Accordingly, it is intended to be bound by the appended claims only, in which:

What is claimed is:

1. Antimicrobial polymeric bisbiguanides capped with alkylene pyrrolidonyl groups.

2. Antimicrobial polymeric bisbiguanides having the formula:

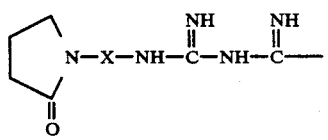

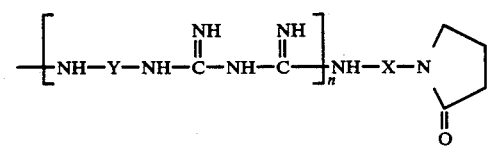

where X is $C_2$–$C_4$ alkylene;
Y is a bivalent bridging group selected from alkylene and alkylene interrupted with oxygen, or cyclic nuclei which may be saturated or unsaturated, and mixtures thereof; and
n is at least 2; and
acid addition salts thereof.

3. Antimicrobial polymeric bisbiguanides according to claim 2 wherein X is a $C_2$ alkylene group.

4. Antimicrobial polymeric bisbiguanides according to claim 2 wherein Y is a $C_2$–$C_{12}$ alkylene group.

5. Antimicrobial polymeric bisbiguanides according to claim 2 wherein Y is $+CH_2CH_2+_6$.

6. Antimicrobial polymeric bisbiguanides according to claim 2 wherein Y is $+CH_2CH_2+_{12}$.

7. Antimicrobial polymeric bisbiguanides according to claim 2 wherein Y is

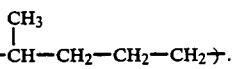

8. Antimicrobial polymeric bisbiguanides according to claim 2 wherein Y is alkylene interrupted by oxygen.

9. Antimicrobial polymeric bisbiguanides according to claim 8 wherein Y is $+CH_2CH_2OCH_2CH_2OCH_2CH_2+$.

10. Antimicrobial polymeric bisbiguanides according to claim 2 wherein said acid addition salt is derived from an inorganic or organic acid.

11. Antimicrobial polymeric bisbiguanides according to claim 2 wherein Y is a mixture of different bridging groups.

12. Antimicrobial polymeric bisbiguanides according to claim 2 wherein n is 2–15.

13. A polymer according to claim 12 wherein n is 4–11.

14. A polymer according to claim 1 wherein Y is a mixture of at least two of:

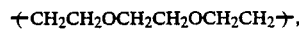

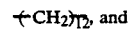

and

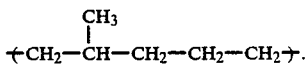

15. A product according to claim 2 wherein compounds having cyano or amino end groups are substantially absent.

16. A process for making antimicrobial bisbiguanide polymers of the formula of claim 2 which comprises condensing a salt of a diamine, $H_2N$-Y-$NH_2$, where Y is a bridging group, with a slight excess over 1:1 stoichiometry of a cyanamide salt, or a bis-cyanoguanidoalkane, where the alkane group is a bridging group and reacting the polymeric intermediate having cyano end groups with a slight excess over stoichiometry of an aminoalkylene pyrrolidone.

17. A process according to claim 16 wherein said cyanamide or bis-cyanoguanidoalkane reactant is present in about a 5–10% excess, and said aminoalkylene pyrrolidone is present in about a 5–10% excess over stoichiometry.

18. A process according to claim 16 wherein the first step is carried out in two stages, the first stage involving a 1:1 stoichiometric reaction between the reactants, followed by a second stage in which the desired excess of the cyanamide or bis-cyanoguanidoalkane starting material is added and reacted with the intermediate of the first stage.

19. A process according to claim 16 wherein the starting material is the cyanamide salt.

20. A process according to claim 16 wherein the starting material is a bis-cyanoguanidoalkane.

21. The product of the process of claim 16.

22. A process according to claim 16 wherein a mixture of diamine salts having different bridging groups are used.

23. A process according to claim 16 wherein a bis-cyanoguanidoalkane is used having a different bridging group than the diamine starting material.

24. A process according to claim 16 wherein said aminoalkylene pyrrolidone reactant is present as the acid salt thereof.

* * * * *